United States Patent
Kobayashi et al.

(10) Patent No.: US 7,741,441 B2
(45) Date of Patent: Jun. 22, 2010

(54) METHOD FOR PRODUCING TYPE IV COLLAGEN

(75) Inventors: Takayuki Kobayashi, Kanagawa (JP); Tasuku Sasaki, Kanagawa (JP); Hayato Miyoshi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 425 days.

(21) Appl. No.: 11/727,573

(22) Filed: Mar. 27, 2007

(65) Prior Publication Data

US 2007/0232787 A1 Oct. 4, 2007

(30) Foreign Application Priority Data

Mar. 28, 2006 (JP) ............................. 2006-086795

(51) Int. Cl.
*C07K 14/00* (2006.01)
(52) U.S. Cl. .......................................... 530/356; 514/2
(58) Field of Classification Search ........................ None
See application file for complete search history.

(56) References Cited

U.S. PATENT DOCUMENTS 6,060,255 A 5/2000 Shibuya et al.

OTHER PUBLICATIONS

Aline Sionkowska, "Thermal stability of UV-irradiated collagen in bovine lens capsules and in bovine cornea", Journal of Photochemistry and Photobiology B: Biology 80(2): 87-92 (2005).*
Sage et al., The Journal of Biological Chemistry, vol. 254, No. 19, Oct. 10, 1979, pp. 9893-9900.

* cited by examiner

*Primary Examiner*—Anand U Desai
(74) *Attorney, Agent, or Firm*—Birch, Stewart, Kolasch & Birch, LLP

(57) ABSTRACT

An object of the invention is to provide type IV collagen without contamination by other proteins and without degradation or denaturation. The present invention provides a type IV collagen which is derived and extracted from lens capsules without the use of an enzyme and has a minimum molecular weight of 160 to 180 kDa measured by SDS-PAGE under reduced conditions.

6 Claims, 1 Drawing Sheet

METHOD FOR PRODUCING TYPE IV COLLAGEN

TECHNICAL FIELD

The present invention relates to type IV collagen having a molecular weight, a structure, and functions equivalent to those of type IV collagen in vivo and a method for producing the same. More particularly, the present invention relates to type IV collagen extracted from animal tissues without the use of an enzyme and a method for extracting type IV collagen from animal tissues without the use of an enzyme.

BACKGROUND ART

Collagen is the most abundant protein in the animal kingdom, accounting for one third or more of all animal proteins. Collagen is a major constituent of connective tissues of animal skin, tendons, bones, and the like. Also, animal bodies are constituted by numerous cells and collagen plays a key role as an intercellular matrix.

Up to the present, as many as about 20 types of genetically different collagen species have been discovered, and differences in properties and functions among them have been demonstrated. Different collagen species are referred to as type I, type II, or the like, and they have been distinguished from one another. It is known that common helical regions of collagen comprising repetitions of Gly-X-Y (wherein X and Y each independently represent any amino acid) are present in the centers of collagen molecules and that triple-helical structures are formed in such regions. Such helical regions of collagen have low immunogenicity and excellent biocompatibility because of the highly conserved sequences thereof among different animal species.

Up to the present, various types of collagens have been extracted from various animal tissues and extensively utilized in the fields of medicine, pharmaceutical products, biochemistry, cosmetics, food, or the like. Depending on the raw material from which collagen is to be extracted, the collagen species to be obtained varies. For example, type I collagen is mainly contained in and extracted from skin, tendons, or bones. Type II collagen is extracted from the cartilage, and type III collagen is extracted from blood vessel walls, for example. Type IV collagen that constitutes the basal membrane is obtained from the placenta or the like. It should be noted that several collagen species might be extracted together from a given raw material.

As a method for extracting collagen, a method involving treatment of materials such as animal bones or skin with an enzyme is known. In such a method, for example, pepsin is allowed to act on such materials in a dilute acetic acid solution. With the extraction method involving use of enzyme treatment, however, a non-helical region of collagen is cleaved with an enzyme. Also, proteins other than collagens that are present in tissues may be eluted from such tissues. Consequently, collagens may be disadvantageously degraded and denatured and a large quantity of proteins other than collagens may be disadvantageously contained in an extract. In order to obtain highly purified collagen, it is necessary to use adequate tissues as raw materials and to prevent contamination by other collagens as much as possible. In order to attain the inherent properties or functions of collagens, collagens that have not undergone degradation or denaturation are required.

Type IV collagen has at its N terminus the 7S domain, which has a triple-helical collagen structure but contains abundant cysteine residues, and at its C-terminus a non-helical region of collagen (NC1 domain). The 7S domain at the N terminus is capable of interacting with the 7S domain and forming a polymer tetrad. At the C terminal NC1, 2 molecules are capable of polymerization. These domains play very important roles for intermolecular interactions of type IV collagen. Unlike other collagens, the helical region of type IV collagen is known to contain 21 Gly-X-Y triplet interruptions. Because of such molecular features, it is very important to extract molecules having all of the functional domains, i.e., the NC1 domain, the 7S domain, and the helical region of collagen, without denaturation or degradation thereof.

In the past, a major raw material for type IV collagen was placenta. Placenta contains abundant collagens other than type IV collagens, such as type I and type V collagens. Accordingly, the placenta is not an optimal raw material from which to extract type IV collagen of high purity. Many methods for extracting type IV collagens are in accordance with the method of Sage et al. (J. Biol. Chem., vol. 254, No. 19, pp. 9893-9900, 1979), which involves solubilization of collagen by pepsin hydrolysis. JP Patent Publication (kokai) No. 11-171898 A (1999) discloses a technique of isolating a polymer fraction of type IV collagen. In this isolation technique, however, type IV collagen is solubilized by pepsin hydrolysis and then extracted, as with the method of Sage et al. With such techniques, type IV collagens having functional domains similar to those in vivo cannot be extracted. Further, collagens have features such that collagen molecules become bound to and aggregated with one another because of the properties of their helical regions. Accordingly, collagen cannot be purified by a technique involving the use of a column that is commonly used for protein purification. Thus, it is very difficult to remove contaminating proteins other than collagens or other collagen species at the time of extraction. Therefore, type IV collagens of high purity have not been obtained.

DISCLOSURE OF THE INVENTION

Conventional methods for producing type IV collagens have suffered from drawbacks such as non-optimal materials, contamination by other proteins, or production of degraded or denatured type IV collagen, due to the extraction techniques involving the use of enzymes. Specifically, it has been difficult to attain properties similar to those of type IV collagens in vivo due to contamination by type I or type V collagens or proteins derived from raw materials, or due to degradation of non-helical regions of collagen at both ends of type IV collagen by enzymes. The present invention is intended to provide type IV collagen without contamination by other proteins and without degradation or denaturation, and it is also intended to provide a method for producing the same.

The present inventors have conducted concentrated studies in order to attain the above objects. As a result, they discovered lens capsules as tissues that contain abundant basement membrane components. Lens capsules are membranes that cover the intraocular lenses, and they are considered to be basal membranes derived from lens epithelial cells, from an embryological point of view. Lens capsules are easily extracted and they contain abundant basal membrane components. Thus, lens capsules are the most in vivo material from which type IV collagen is extracted. As a result of concentrated studies, the present inventors discovered a method for producing type IV collagen from lens capsules that contain abundant basal membrane components without the use of an enzyme. Further, separation and concentration of type IV collagen with the use of salt enabled removal of other proteins or degradation products. Type IV collagen that had been obtained by such method had satisfactory quality of high purity and of less degradation or denaturation and was highly concentrated. The present invention has been completed based on such findings.

Specifically, the present invention provides a type IV collagen which is derived and extracted from lens capsules without the use of an enzyme and has a minimum molecular weight of 160 to 180 kDa measured by SDS-PAGE under reduced conditions.

Preferably, type IV collagen of the present invention has intermolecular interactive domains at one of or both ends of a polypeptide chain.

Preferably, type IV collagen of the present invention has Gly-Xaa-Xbb (wherein Xaa and Xbb each independently represent any amino acid residue) repeats in the polypeptide chain molecule.

Another aspect of the present invention provides a method for producing type IV collagen of the present invention, wherein collagen is extracted from lens capsules of an animal without the use of an enzyme.

Preferably, the method for producing type IV collagen of the present invention comprises at least steps of: (1) agitating lens capsules in a phosphate buffered saline to recover a precipitate; (2) agitating the precipitate obtained in step (1) in an aqueous acidic solution to recover a supernatant containing type IV collagen; and (3) adding salt to the supernatant obtained in step (2) to allow type IV collagen to precipitate and recovering the resulting precipitate.

Preferably, steps (1) to (3) are carried out at a low temperature.

Preferably, the phosphate buffered saline used in step (1) contains a protease inhibitor.

Preferably, the aqueous acidic solution used in step (2) contains a protease inhibitor.

In step (3), preferably, salt is added to the supernatant obtained in step (2) and type IV collagen is then allowed to precipitate by centrifugation.

Preferably, the method of the present invention further comprises step (4) of solubilizing the precipitate obtained in step (3) with an aqueous acidic solution and then dialyzing the resultant with an aqueous acidic solution.

A further aspect of the present invention provides type IV collagen derived from lens capsules which is produced by the method of the present invention and which has a minimum molecular weight of 160 to 180 kDa measured by SDS-PAGE under reduced conditions.

PREFERRED EMBODIMENTS OF THE INVENTION

Figure 1:
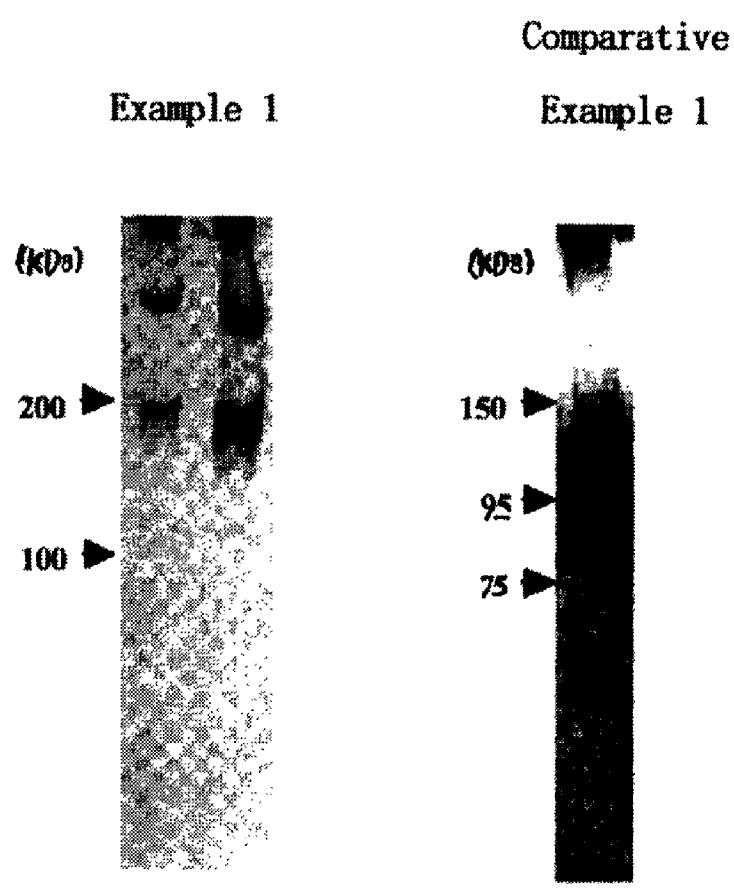
FIG. 1 shows the results of SDS-PAGE analysis of type IV collagen obtained in Example 1 and in Comparative Example 1. In the left diagram, the left lane indicates type IV collagen obtained from porcine eyeballs and the right lane indicates type IV collagen obtained from bovine eyeballs.

Hereafter, the present invention is described in greater detail.

The type IV collagen derived from lens capsules of the present invention is extracted from lens capsules without the use of an enzyme. Such collagen has a minimum molecular weight of 160 to 180 kDa measured by SDS-PAGE under reduced conditions.

In the present invention, the "lens capsules" are membranous constructs that cover the intraocular lens and they are considered to be basal membranes derived from lens epithelial cells, from an embryological point of view.

In the present invention, the term "reduced conditions" refers to conditions whereby at least some of intramolecular or intermolecular disulfide bonds of type IV collagen are reduced and become uncrosslinked. Under such conditions, for example, a reducing agent such as β-mercaptoethanol or dithiothreitol and a buffer containing sodium dodecyl sulfate are added and the resultant is then heated at 70° C. or higher for at least 1 minute.

The type IV collagen derived from lens capsules of the present invention preferably has intermolecular interactive domains at one of or both ends of a polypeptide chain. The term "intermolecular interactive domains" used herein refers to a polypeptide region that is required for physical polypeptide-polypeptide bonds.

The type IV collagen derived from lens capsules of the present invention preferably has Gly-Xaa-Xbb (wherein Xaa and Xbb each independently represent any amino acid residue) repeats in the polypeptide chain molecule.

Further, the present invention relates to a method for producing type IV collagen of the present invention which comprises extracting collagen from lens capsules of an animal without the use of an enzyme. More specifically, the method for producing type IV collagen of the present invention preferably comprises at least steps of: (1) agitating lens capsules in a phosphate buffered saline to recover a precipitate; (2) agitating the precipitate obtained in step (1) in an aqueous acidic solution to recover a supernatant containing type IV collagen; and (3) adding salt to the supernatant obtained in step (2) to allow type IV collagen to precipitate and recovering the resulting precipitate.

Steps (1) to (3) can be carried out at a low temperature. The term "low temperature" preferably refers to 4° C. or lower in the present invention.

The phosphate buffered saline used in step (1) and/or the aqueous acidic solution used in step (2) preferably comprise protease inhibitors. The term "protease inhibitor" used herein is a generic term for a substance that inhibits peptide hydrolases. Examples thereof include acetyl-pepstatin, AEBSF, ALLM, ALLN, amastatin, ε-amino-n-caproic acid, aminopeptidase N inhibitor, $\alpha_1$-antichymotrypsin, antipain, $\alpha_2$-antiplasmin, $\alpha_2$-antiplasmin, antithrombin III, $\alpha_1$-antitrypsin, p-APMSF, aprotinin ATBI, benzamidine, bestatin, calpastatin, calpeptin, carboxypeptidase inhibitor, caspase inhibitor, cathepsin inhibitor, chymostatin, chymotrypsin inhibitor, cystat, 1,5-dansyl-Glu-Gly-Arg chloromethyl ketone, 3,4-dichloroisocoumarin, diisopropylfluorophosphate, dipeptidylpeptidase, E-64 protease inhibitor, ecotin, EDTA, EGTA, elastase inhibitor, elastatinal, EST, FUT-175, GGACK, 2-guanidinoethylmercaptosuccinic acid, HDSF, α-iodoacetamide, kininogen, leupeptin, $\alpha_2$-macroglobulin, pepstatin A, phenylmethylsulfonyl fluoride, phosphoramidon, PPACK, prolyl endopeptidase inhibitor, serine protease inhibitor, tripeptidylpeptidase II inhibitor, trypsin inhibitor, and D-Val-Phe-Lys chloromethyl ketone.

Hereafter, the method for producing type IV collagen of the present invention is described in greater detail. In the present invention, eyeballs of other vertebrates including animals used for meat such as bovines or pigs, fishes, or amphibians can be used as raw materials. Flesh adhering to the eyeballs is removed by surgical operations to extract corneas. Lenses are extracted from the eyeballs, and insoluble matters such as vitreous bodies adhering to the lenses are substantially completely removed. After the removal of insoluble matters, lens capsules are soaked in a cold phosphate buffered saline (PBS). A phosphate buffered saline (PBS) contains 1.54 mM potassium phosphate monobasic, 155.17 mM sodium chloride (NaCl), and 2.71 mM sodium phosphate dibasic (pH 7.2). Cold PBS is maintained preferably at 0° C. to 15° C., more preferably at 0° C. to 10° C., and most preferably at 0° C. to 4° C. Cold PBS preferably comprises a protease inhibitor. As protease inhibitors, at least 1, preferably at least 3, and more preferably at least 5 types of the protease inhibitors selected from among phenylmethylsulfonyl fluoride, N-ethylmaleimide, EDTA, aprotinin, bestatin, and calpain inhibitors can be added. The lens capsules are agitated in cold PBS and insoluble matters adhering to the lens capsules are removed. Thereafter, the lens capsules are recovered by centrifugation. Centrifugation can be carried out at 100 to 20,000 g, preferably at 1,000 to 10,000 g, and more preferably at 2,000 to 8,000 g.

Subsequently, the precipitated lens capsules are agitated in an aqueous acidic solution. The aqueous acidic solution that can be used in the present invention preferably comprises a protease inhibitor. The aqueous acidic solution that can be used in the present invention has a pH of 1.0 to 5.0, and preferably a pH of 2.0 to 4.0. The aqueous acidic solution may be comprised of organic acids or mineral acids, and examples thereof include hydrochloric acid, sulfuric acid, acetic acid, and citric acid. A pH level of an aqueous acidic solution that is outside the above-mentioned range is not preferable since it results in a lowered yield. As protease inhibitors, at least 1, preferably at least 3, and more preferably at least 5 protein inhibitors selected from among the aforementioned protease inhibitors can be used. After the lens capsules are introduced into the aqueous acidic solution, the lens capsules are agitated at 0° C. to 15° C., preferably at 0° C. to 10° C., and more preferably at 0° C. to 4° C., for 1 to 7 days, and preferably 2 to 5 days, to extract collagen that is soluble in an aqueous acidic solution. Acid-soluble collagen dissolved in an aqueous acidic solution can be separated from the residue by a conventional physical technique. In general, centrifugation is preferably employed. An aqueous acidic solution can be further added to the residue to repeat extraction by techniques similar to those described above.

As an example of a method that is employed in a step of allowing the acid-soluble collagen from which the residue has been separated to precipitate and recovering the same, salt may be added to increase the salt concentration and to allow the collagen to precipitate. Salt to be added contains sodium or potassium. Sodium chloride, potassium chloride, or the like can be generally used. The salt concentration is 0.1 to 3.0 M, preferably 0.25 to 2.5 M, and more preferably 0.5 to 2.0 M. Collagen precipitated with the aid of salt is recovered by centrifugation and then solubilized with an aqueous acidic solution, for example.

The resulting collagen solution is introduced into a dialysis tube, and the solution is dialyzed with an aqueous acidic solution while agitating at 0° C. to 15° C., preferably at 0° C. to 10° C., and more preferably at 0° C. to 4° C., for 1 to 5 days and preferably for 2 to 3 days. After dialysis, highly purified, undenatured, and undegraded type IV collagen can be obtained.

The type IV collagen derived from lens capsules of the present invention can be utilized in fields relating to food, pharmaceutical products or medicine, cosmetics, or the like. The type IV collagen derived from lens capsules of the present invention can be used as a material for confectionaries, such as jelly, cosmetic ingredients, drug capsules, artificial skin, vehicles for bone treatment, prosthetic material for surgery (e.g., suture thread or gauze), or carriers for cell cultures, for example.

The present invention is hereafter described in greater detail with reference to the following examples, although the technical scope of the present invention is not limited thereto.

EXAMPLES

Example 1

In accordance with the following procedures (1) to (16), 16 mg and 8 mg of purified polymeric type IV collagens were obtained from raw materials, i.e., bovine and porcine eyeballs, respectively. The following procedures were carried out at 4° C.

(1) Removing corneas from eyeballs using scissors and extracting lenses from intraocular eyeballs.

(2) Removing insoluble matter such as vitreous bodies adhering to the lenses using scissors to as great an extent as possible.

(3) Adding a tablet of complete protease inhibitor cocktails (Roche) to 50 ml of cold PBS (phosphate buffered saline), allowing the tablet to dissolve therein, and introducing lens capsules thereinto, followed by agitation for 2 hours.

(4) Removing insoluble matter in the supernatant by centrifugation (2,000 g for 10 minutes at 4° C.).

(5) Suspending the precipitate in 25 ml of a 0.5 M acetic acid solution comprising a half tablet of complete protease inhibitor cocktails (Roche) dissolved therein.

(6) Finely grinding the lens capsules using a homogenizer (IKA).

(7) Agitating the finely ground lens capsules for 3 days to extract type IV collagen.

(8) Separating the supernatant (acetic acid-soluble collagen) from the precipitate by centrifugation (2,000 g for 10 minutes at 4° C.).

(9) Repeating the procedure of extraction by agitation and centrifugation again.

(10) Adding NaCl, the crystals of which have been ground in a mortar to as great an extent as possible, to the supernatant resulting from centrifugation to result in a final concentration of 1.7 M.

(11) Agitating the resultant overnight to allow collagen to precipitate.

(12) Recovering the precipitate by centrifugation (5,000 g for 30 minutes at 4° C.).

(13) Adding 0.5M acetic acid to the precipitate for thorough dissolution.

(14) Introducing an aqueous acidic collagen solution into a dialysis tube (Sanko Junyaku Co., Ltd.) and performing dialysis using 0.5 M acetic acid.

(15) Performing dialysis with 2 mM hydrochloric acid.

(16) Recovering the dialyzed collagen solution to obtain a solution of purified type IV collagen.

Comparative Example 1

In accordance with the following procedures (1) to (8), type IV collagen was obtained from a raw material, i.e., placenta. The following procedures were carried out at 4° C.

(1) Slicing the placenta into 1-cm-square pieces with scissors.

(2) Introducing the placenta into cold PBS (phosphate buffered saline), followed by agitation.

(3) Recovering the precipitate by centrifugation (5,000 g for 30 minutes at 4° C.).

(4) Adding 0.4 M sodium acetate to the precipitate and washing the resultant until all blood components are eliminated.

(5) Recovering the precipitate by recentrifugation and then washing the resultant with 0.5 M formic acid.

(6) Suspending the precipitate in 0.5 M formic acid and then adding pepsin to a final concentration of 420 unit/ml.

(7) Performing extraction with agitation at 8° C. to 110° C. for 16 hours.

(8) Subjecting the enzyme-processed product to centrifugation to recover the supernatant.

Test Example 1 (Analysis)

Type IV collagen obtained in Example 1 was subjected to sodium dodecyl sulfate-polyacrylamide electrophoresis (SDS-PAGE) (the left diagram shown in FIG. 1) and to amino acid analysis. Under reduced conditions on SDS/PAGE (equivalent amounts of 2× Laemmli sample buffer, 62.5 mM Tris-HCl (pH 6.8), 2% SDS, 12.5% glycerol, 0.01% Bromophenol Blue, and 10% 2-mercaptoethanol were mixed and the resultant was then heated at 90° C. for 5 minutes), a 150-180 kDa band, and bands showing an apparent molecular weight arising from crosslinking of two or more molecules of collagen, were observed. Under nonreduced conditions (equivalent amounts of 2× Native sample buffer, 62.5 mM Tris-HCl (pH 6.8), 2% SDS, 40.0% glycerol, and 0.01% Bromophenol Blue were mixed and the resultant was then heated at 90° C. for 5 minutes), electrophoresis did not substantially take place. Contamination with collagen other than type IV collagen or any other proteins was not observed. Also, type IV collagen obtained in Comparative Example 1 was analyzed by SDS-PAGE (the right diagram shown in FIG. 1).

As described above, collagen obtained in Example 1 (the present invention) had a higher molecular weight than that obtained in Comparative Example 1. With the method of Example 1, type IV collagen could be extracted from lens capsules without the use of an enzyme because of the use of salt separation.

INDUSTRIAL APPLICABILITY

According to the present invention, type IV collagen can be extracted from optimal materials, i.e., lens capsules, without the use of an enzyme. Thus, type IV collagen can be produced without degradation or denaturation. According to the present invention, therefore, type IV collagen similar to that in vivo can be extracted from lens capsules.

The invention claimed is:

1. A method for producing a type IV collagen which is derived and extracted from lens capsule without the use of an enzyme and has a minimum molecular weight of 160 to 180 kDa measured by SDS-PAGE under reduced conditions, wherein collagen is extracted from lens capsules of an animal without the use of an enzyme, which comprises at least steps of: (1) agitating lens capsules in a phosphate buffered saline to recover a precipitate; (2) agitating the precipitate obtained in step (1) in an aqueous acidic solution to recover a supernatant containing type IV collagen; and (3) adding salt to the supernatant obtained in step (2) to allow type IV collagen to precipitate and recovering the resulting precipitate.

2. The method of claim 1, wherein steps (1) to (3) are carried out at a low temperature.

3. The method of claim 1 or 2, wherein the phosphate buffered saline used in step (1) contains a protease inhibitor.

4. The method of claim 1, wherein the aqueous acidic solution used in step (2) contains a protease inhibitor.

5. The method of claim 1, wherein, in step (3), salt is added to the supernatant obtained in step (2) and type IV collagen is then allowed to precipitate by centrifugation.

6. The method of claim 1, which further comprises step (4) of solubilizing the precipitate obtained in step (3) with an aqueous acidic solution and then dialyzing the resultant with an aqueous acidic solution.

* * * * *